United States Patent [19]

Zepp

[11] Patent Number: 5,211,885
[45] Date of Patent: May 18, 1993

[54] SQUARYLIUM DYES AND PRODUCTS AND PROCESSES USING SAME

[75] Inventor: Charles M. Zepp, Berlin, Mass.

[73] Assignee: Steadfast Inc., Cambridge, Mass.

[21] Appl. No.: 716,250

[22] Filed: Jun. 17, 1991

[51] Int. Cl.$^5$ ............... F21V 9/04; C07D 265/02
[52] U.S. Cl. ................................. 252/587; 544/73
[58] Field of Search ............ 252/582, 587; 544/73, 544/99

[56] References Cited

U.S. PATENT DOCUMENTS

| | | | |
|---|---|---|---|
| 5,013,474 | 5/1991 | Arai et al. | 252/299.1 |
| 5,024,911 | 6/1991 | Akasaki et al. | 430/58 |
| 5,030,009 | 7/1991 | Ando et al. | 252/582 |
| 5,104,758 | 4/1992 | Mashimo et al. | 430/73 |
| 5,145,774 | 9/1992 | Tarnowski et al. | 252/582 |
| 5,149,819 | 9/1992 | Satoh et al. | 548/149 |
| 5,153,085 | 10/1992 | Akasaki et al. | 430/58 |

*Primary Examiner*—Robert L. Stoll
*Assistant Examiner*—Philip Tucker
*Attorney, Agent, or Firm*—Alvin Isaacs

[57] ABSTRACT

A novel class of squarylium infrared absorbing dyes is disclosed which are prepared by the condensation of squaric acid with a benzoxazinone. The dyes are unique in that they possess the desirable properties of squarylium dyes in general along with a narrow band of peak absorbency greater than 1000.

Because of their stability to laser beams, the dyes are particularly useful in ocular products for eye protection against lasers.

10 Claims, No Drawings

SQUARYLIUM DYES AND PRODUCTS AND PROCESSES USING SAME

BACKGROUND OF THE INVENTION

The prior art is replete with references to dyes which absorb in the infrared region of the visible spectrum. Such dyes find usefulness in such diverse fields as sensitizers for infrared sensitive phototgraphic emulsions, absorbers for optical storage systems, filters for infrared light, as laser dyes, etc.

Although there are many classes of dyes which absorb in the infrared, squarylium dyes, the class of dyes made by condensation of squaric acid (3,4-dihydroxy-3-cyclobutene-1,2-dione) are of particular interest due to their properties, e.g. narrow absorptive band, high molar absorptivity, relative stability and minimal absorption of visible light.

However, as a class squarylium dyes absorb in the region of between about 500 to about 800 nanometers.

As the use of lasers has rapidly increased in recent years, so has the demand for laser-protective eyewear. The traditional methodology has been the use of color filter glass elements. However, these filters suffer from various severe shortcomings, including a broader bandwidth than is desired, limited transmission in the red spectral region, etc.

While squarylium dyes as a class do not suffer from these disadvantages, for protection against certain of the lasers in vogue today it is necessary that the dye possess peak absorption in a band in excess of 1000 nanometers, e.g. have a peak absorption of on the order of about 1055 nanometers in methylene chloride.

Stated simply, the task of this invention is to provide squarylium dyes which will possess a peak absorption in excess of 1000 nanometers in methylene chloride and which are further characterized by possessing a sharp peak, stability against degradation of protective absorbtivity upon contact with lasers, and minimal absorption of visible light whereby the dyes are characterized as being "clean".

BRIEF DESCRIPTION OF THE INVENTION

In accordance with the present invention, this task is solved by providing a novel class of dyes prepared by the condensation of squaric acid with a benzoxazinone.

The novel dyes of this invention may be represented by the formula:

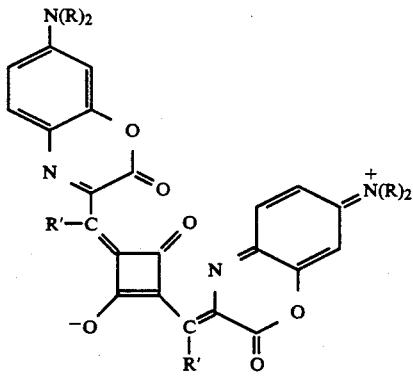

(I)

wherein:
each R, which may be the same or different, is hydrogen, alkyl having 1 to 4 carbon atoms or phenyl, including phenyl radicals substituted by one or more alkyl radicals, e.g. methylphenyl, 2,4-dimethylphenyl, 2,4,6-trimethylphenyl, etc.; and each R', which may be the same or different, is hydrogen, alkyl having 1 to 6 carbon atoms, phenyl or phenalkyl.

Preferred are those dyes which are symmetrical in which each R is alkyl of 1 to 4 carbon atoms and each R' is hydrogen.

DETAILED DESCRIPTION OF THE INVENTION

As was heretofore mentioned, the present invention is particularly directed to novel infrared (IR) absorbing dyes or optical filter agents for protecting the eyes from lasers. Accordingly, for a clear understanding of the nature and objects of the invention, it will be described in detail hereinafter by reference thereto.

Lasers [the acronym for light amplification by stimulated emission of radiation] are devices which transform various frequencies into extremely intense, small and nearly nondivergent beams of monochromatic radiation in the visible region with all the waves in phase.

They have found increased usage, for example, in medical and military applications. This increased usage in turn creates increasing need in such applications for means to protect the eyes as well as radiation sensors and the like from damaging laser radiation.

Products of this nature are heretofore known in the art. While not intended to be an exhaustive search of the prior art, the following patents resulting from a cursory search are nevertheless considered to be illustrative of the state of the art.

U.S. Pat. No. 4,933,110 issued to Tucker discloses optical light filters, useful for eye protection from lasers of at least six types having a range of different wavelengths, as distinguished from what the patentee states to be most prior art laser radiation shields which are designed for narrow band selective absorption at the specific wavelength of a single type of laser, or in some instances at specific wavelengths of two or three lasers. According to the invention, this is accomplished by providing a radiation shield in which a combination of four absorbers are disposed in a transparent medium, preferably polycarbonate. The four absorbers are: (1) a vanadyl phthalocyanine sulfonamide absorber; (2) an ultraviolet absorber having broad band absorption in the UV band; (3) an absorber having a broad absorption band at the blue to green end of the spectrum; and (4) a narrow band infrared absorber having maximum absorption near 980 nm, such as tris(p-diethylaminophenyl)aminium hexafluoroantimonate, tris(p-diethylaminophenyl)aminium hexafluoroarsenate, tris(p-dibutylaminophenyl)aminium hexafluoroantimonate and tris(p-dibutylaminophenyl)aminium hexafluoroarsenate.

In Table 2 bridging Cols. 3,4 of the patent, the concentrations of the specified absorbers recited in the previous Examples are said to provide specified optical densities of 2or more for lasers ranging from 488 nm to 1064. Included in this listing are optical densities of 4 for both Nd glass (1060 nm) and Nd YAG (1064 nm).

However, the patented invention is stated to provide this protection while maintaining luminous transmission of only "at least 12% and up to 25% or more".

U.S. Pat. No. 4,935,166 issued to Lee et al discloses a solid state form of a dye-solution filter wherein physical vapor depositable dyes are codeposited with a polyester matrix in a vacuum system to randomly disperse dye molecules in a solid diluent. The dyes are selected to absorb at the wavelength of interest. Dilution in a transparent matrix is said to afford narrow band absorption and good out of band transmittance. Multilayer configurations allow absorption of a plurality of wavelengths. At the bottom of Col. 2, suitable dyes were said to be the porphrins, metallophthalocyanines or rare-earth diphthalocyanines, cyanines or carbocyanines, merocyanines, squaryliums, and tetracenes.

In Col. 3. particular interest is said to be in an absorption filter which absorbs at both 530 nm and 694 nm.

As distinguished from the objectives of these patents, the task of the present invention is directed to providing a dye which is characterized as being "clean" or substantially transparent to visible light in the blue-red regions of the spectrum and which will provide protection against those powerful lasers whose primary output is in excess of 1000, e.g. in the range of, say, 1000 to 1100 nm.

In accordance with the present invention this task is solved by providing a novel class of squarylium dyes of the formula:

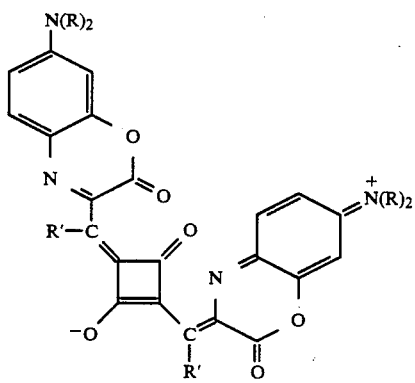

(I)

wherein:

each R, which may be the same or different, is hydrogen, alkyl having 1 to 4 carbon atoms or phenyl, including phenyl radicals substituted by one or more alkyl radicals, e.g. methylphenyl, 2,4-dimethylphenyl, 2,4,6-trimethylphenyl, etc.; and each R', which may be the same or different, is hydrogen, alkyl having 1 to 6 carbon atoms, phenyl or phenalkyl.

Preferred are those dyes which are symmetrical and in which each R is alkyl of 1 to 4 carbon atoms and each R' is hydrogen.

Dyes of the foregoing description may be prepared by condensing squaric acid (II) with a benzoxazinone (III) as illustrated below:

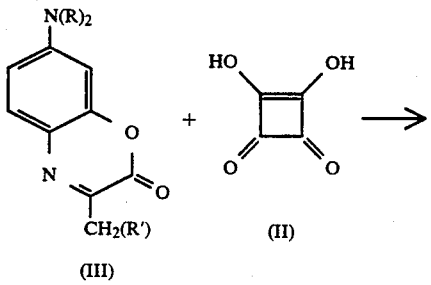

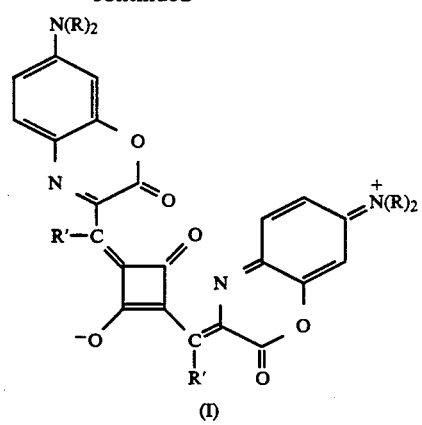

(I)

As reported in the literature and well understood in the art, condensation reactions with squaric acid and an active compound are generally conducted under conditions for removing water from the reaction mixture. For example, the condensation may be carried out under reflux in an alkanol/benzene solvent mixture. The present condensation reaction illustrated above is also performed in the presence of a hindered base such as quinoline in order to pull a proton off the —CH$_2$— moiety of the benzoxazinone (III).

The following compounds are illustrative of the novel dyes of this invention, i.e. IR absorbers within the scope of Formula I.

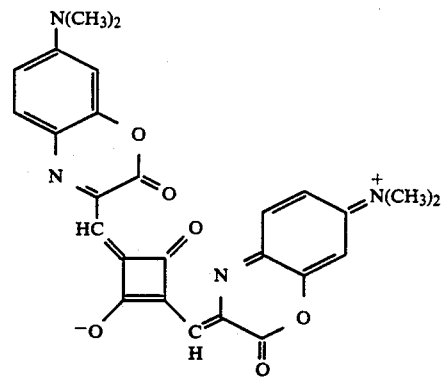

(1)

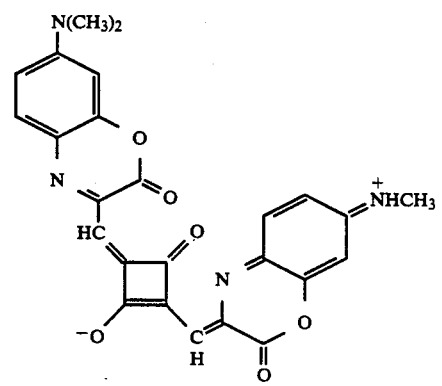

(2)

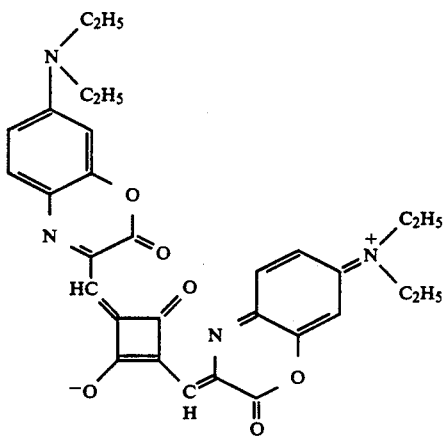 (3)
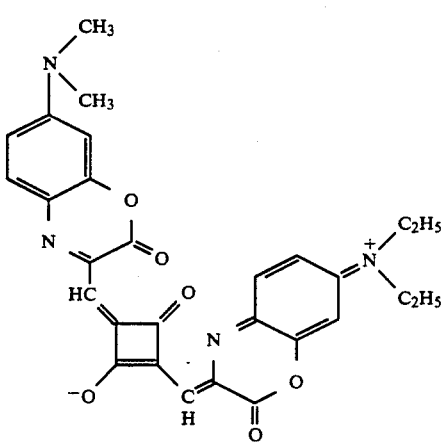 (4)
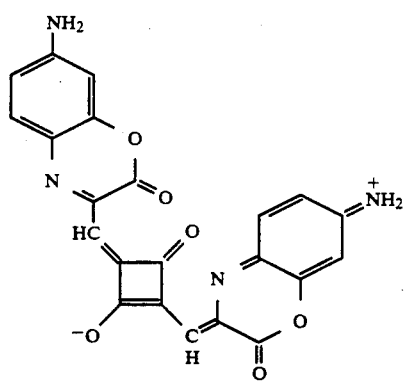 (5)
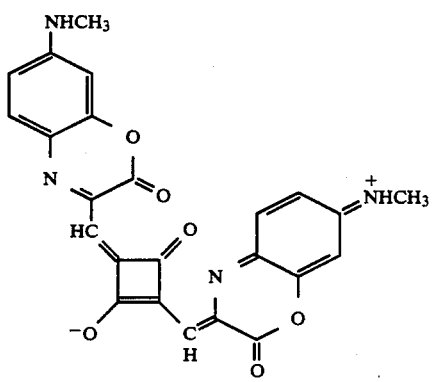 (6)
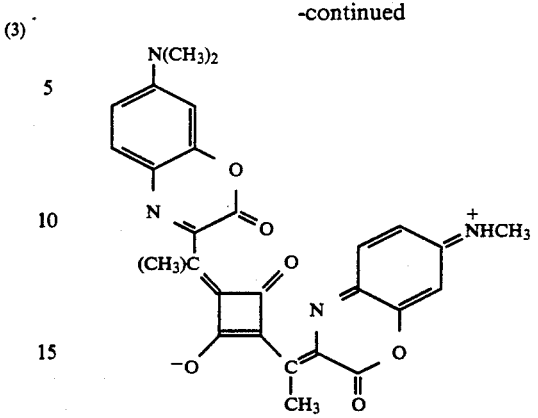 (7)
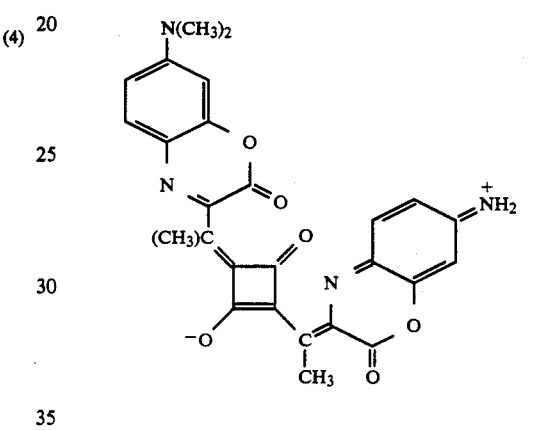 (8)
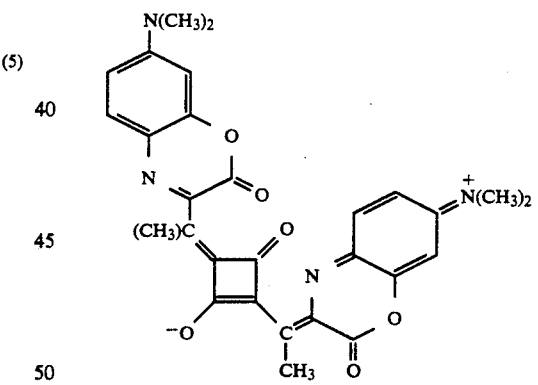 (9)
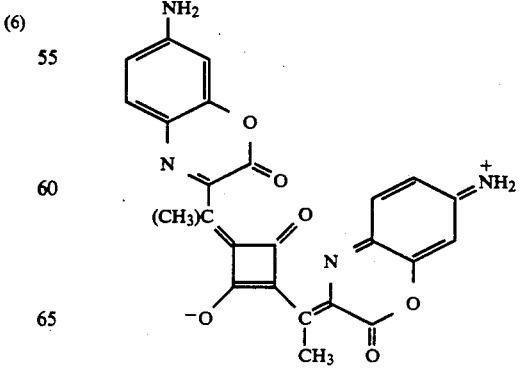 (10)

-continued

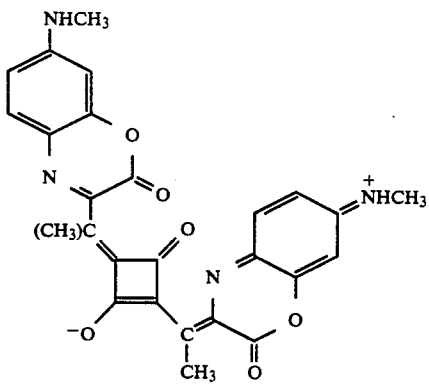 (11)

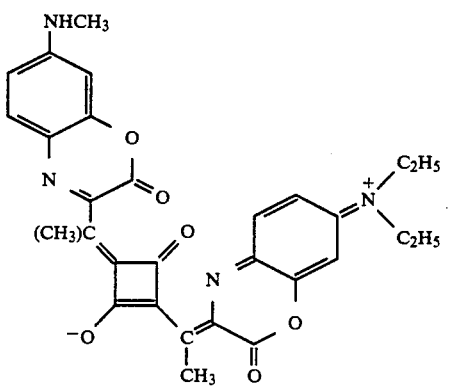 (12)

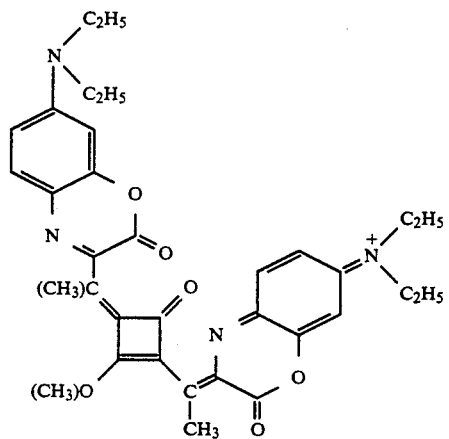 (13)

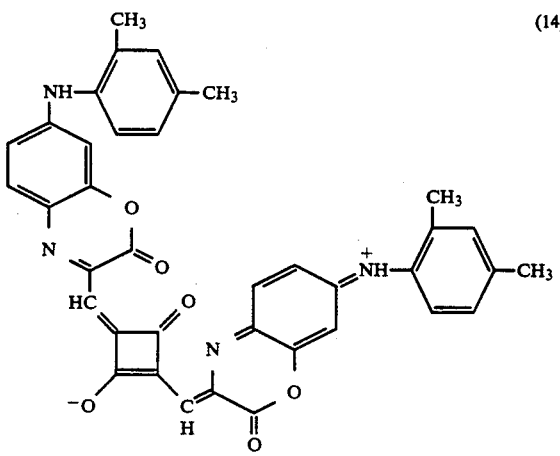 (14)

-continued

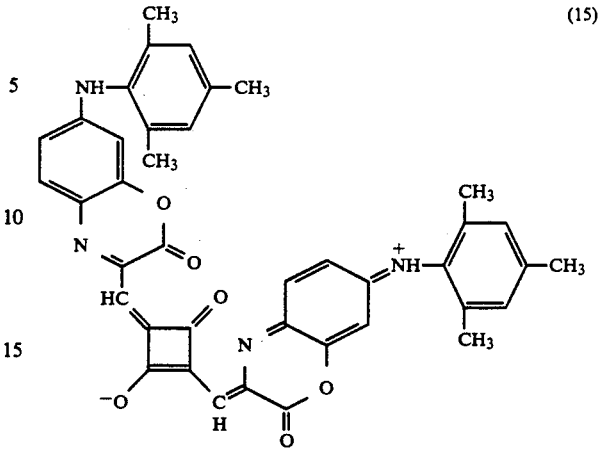 (15)

The following example shows by way of illustration and not by way of limitation the preparation of the novel dyes of this invention.

EXAMPLE 1.16 gms. (0.005 mole) of 1-dimethylamino-4-methyl-benzoxazinone (the compound of Formula III wherein each R is methyl and each R' is hydrogen), 0.285 gm. (0.0025 mole) of squaric acid, and 0.5 ml. of quinoline were stirred in 15 mls. of 1-butanol and 15 mls. of benzene. The mixture was heated and allowed to reflux for 24 hours. Water which formed during the condensation was removed by use of a Dean-Stark trap. After cooling, the dye was isolated as a brown solid by filtration. In this manner, 0.13 gm. of the dye of formula 1 was obtained. The dye exhibited spectral absorption with a $\lambda max = 1055$. The dye is characterized as having a narrow absorption band and being substantially transparent to light in the visible range of 400–700 nms. (blue to red light).

As heretofore mentioned, the novel dyes of this invention find particular use as optical filter agents in plastic optical elements for protecting the eyes from harmful laser radiation, the primary output of which is in the range of on the order of 1000 to 1100 nms.

These optical elements may, for example, comprise a suitable transparent polymeric matrix in which the dye is dispersed and then cast or molded to form the shaped optical element.

Suitable polymeric materials for the purpose are well known in the art and per se comprise no part of this invention. Accordingly, their selection will be a matter of choice within the expected judgment of the skilled worker. However, for purposes of illustration, suitable transparent polymeric matrices will include polycarbonates, polyvinyl or polyvinylidene halides, homopolymers and copolymers of acrylonitrile and styrene, acrylic resins, cellulose esters such as cellulose propionate, etc. The preferred polymeric materials are the polycarbonates, e.g. a bisphenol-A polycarbonate, preferably one that is free of acidic or basic residues.

In lieu of incorporating the dye in the polymeric material employed to provide the shaped article, the dye may instead be applied as a coating in a suitable transparent vehicle or dispersed in a transparent film which is then laminated to one surface of the article for protecting against the laser.

In any case, the optical element containing the novel dyes of this invention may be cast or molded to provide sheets, lenses, eyeglasses, films, shields and the like. The dyes may be employed in these elements alone or in combination with one or more other dyes, e.g. those heretofore known in the art, providing protection against lasers in other selected bands of the spectrum.

The amount of the dye to be incorporated will in part be dependent upon the efficiency of the dye and will in part be dependent upon the weight of the polymeric material in which it is dispersed. Accordingly, it is not capable of precise quantification. In general, ranges of on the order of from about 0.1 to about 0.20 percent by weight of the matrix material to provide an optical density (absorbance) of on the order of at least 4.0 are contemplated. In any case, the dye should be present in an "effective amount", "effective" as used herein and in the appended claims being defined as being an amount sufficient to provide the desired protection against lasers at the absorption peak of the dye.

By way of recapitulation, the present invention provides a novel class of IR absorbing dyes having peak absorption in excess of 1000 nm. While capable of the various uses to which IR absorbers may be employed, they find particular efficacy in plastic elements for providing protection against harmful laser radiation within the band that they provide absorption. The dyes are characterized as having a narrow band of peak absorption and as being substantially clean or transparent to visible light, i.e. light within the blue to red regions of the visible light spectrum. The dyes are further characterized as being stable against degradation to lose its absorptive characteristics upon contact with laser radiation and as a class are generally thermally stable as well.

Since certain changes may be made without departing from the scope of the invention herein contemplated, it is intended that all matter contained in the foregoing description, including the specific example, be taken as illustrative and not in a limiting sense. Accordingly, the invention is limited only as indicated in the appended claims.

What is claimed is:

1. An infrared absorbing dye of the formula:

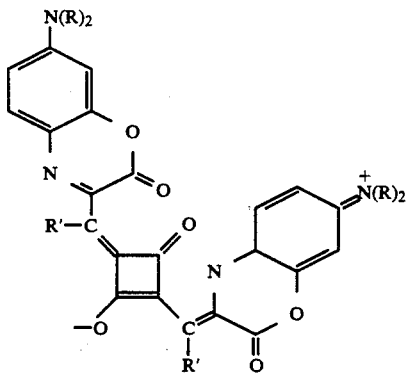

wherein:
each R is hydrogen, alkyl having 1 to 4 carbon atoms or phenyl, including phenyl radicals substituted by one or more alkyl radicals; and
each R' is hydrogen, alkyl having 1 to 6 carbon atoms, phenyl or phenalkyl.

2. A dye as defined in claim 1 wherein said dye is symmetrical.
3. A dye as defined in claim 1 wherein each R is the same.
4. A dye as defined in claim 1 wherein each R is alkyl.
5. A dye as defined in claim 1 wherein each R is methyl.
6. A dye as defined in claim 1 wherein each R' is hydrogen.
7. A dye as defined in claim 6 wherein each R is alkyl and each of the alkyls is the same.
8. A dye as defined in claim 1 wherein the dye is:

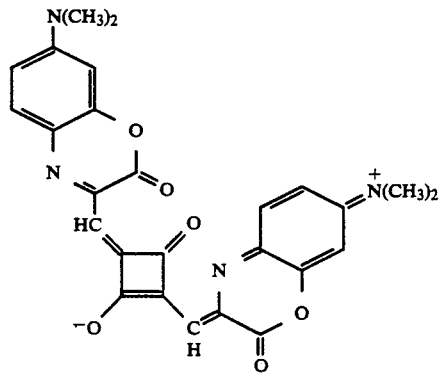

9. A dye as defined in claim 1 wherein the dye is:

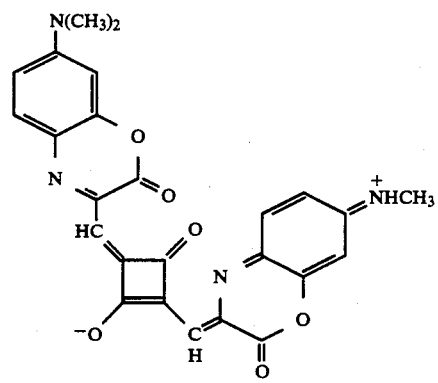

10. A dye as defined in claim 1 wherein the dye is:

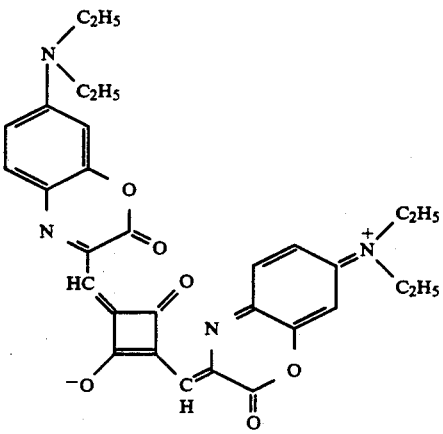

* * * * *